US005591824A

United States Patent [19]
Ziai et al.

[11] Patent Number: 5,591,824
[45] Date of Patent: Jan. 7, 1997

[54] PORCINE APAMIN BINDING PROTEIN/RECEPTOR

[75] Inventors: Mohammad R. Ziai, Montvale; Patricia T. Sokol, Bedminster; Manik Chandra, Paramus, all of N.J.

[73] Assignee: American Cyanamid Company, Wayne, N.J.

[21] Appl. No.: 229,511

[22] Filed: Apr. 21, 1994

Related U.S. Application Data

[63] Continuation-in-part of Ser. No. 922,307, Jul. 30, 1992, abandoned, and Ser. No. 923,095, Jul. 30, 1992, Pat. No. 5,401,652.

[51] Int. Cl.$^6$ .................................................. C07K 14/705
[52] U.S. Cl. ............................ 530/350; 435/69.1; 514/2; 536/23.5
[58] Field of Search .................................. 530/350, 388.2; 435/69.1; 514/2

[56] References Cited

PUBLICATIONS

Defendini et al, *Mol. Immun.* 27(6):551–558, 1990.
Leveque et al., *FEBS LETTS* 275(1,2):185–189, Nov. 1990.
Kelleher et al, *Cell* 69:55–65, 03 Apr. 1992.
Silberstein et al., *J. Biol. Chem* 267(33):23658–23663, 25 Nov. 1992.
Rudy, B., "Diversity and Ubiquity of K Channels," *Neuroscience*, 25:729–749 (1988).
Castle, N. A., et al., "Toxins in the Characterization of Potassium Channels," *TINS* 12:59–65 (1989).
Haylett, B. G. et al., "Calcium–activated Potassium Channels," In Cook, N. S. (ed.), Ellis Horwood Ltd., 70–95 (1990).
Latorre, R., et al., "Varieties of Calcium–Activated Potassium Channels," *Annu. Rev. Physiol.*, 51:385–399 (1989).
Pennefather, P., et al., "Two Distinct Ca–Dependent K Currents in Bullfrog Sympathetic Ganglion Cells," *Proc. Natl. Acad. Sci., USA*, 82:3040–3044 (1985).
Marty, A., "The Physiological Role of Calcium–Dependent Channels," *TINS*, 12:420–424 (1989).
Lancaster, B., et al., "Calcium Activates Two Types of Potassium Channels in Rat Hippocampal Neurons in Culture," *J. Neurosci.*, 11:23–30 (1991).
Strong, P. N., "Potassium Channel Toxins," *Pharmac. Ther.*, 46:137–162 (1990).
Saunders, H. H., et al., "Spontaneous Transient Outward Currents and CA++–Activated K+ Channels in Swine Tracheal Smooth Muscle Cells," *J. Pharmacol. Exp. Ther.*, 257:1114–1119 (1991).
Moczydlowski, E. et al., "An Emerging Pharmacology of Peptide Toxins Targeted Against Potassium Channels,"*J. Membrane Biol.*, 105:95–111 (1988).
Blatz, A. L. et al., "Ion Conductance and Selectivity of Single Calcium–activated Potassium Channels in Cultured Rat Muscle," *J. Gen. Physiol.*, 84:1–23 (1984).
Blatz, A. L., et al., "Single Apamin–blocked Ca–activated K+ Channels of Small Conductance in Cultured Rat Skeletal Muscle," *TINS*, 10:463–467 (1987).

Blatz, A. L., et al., "Calcium–Activated Potassium Channels," *TINS*, 10:463–467 (1987).
Habermann, E., et al., "Bee Venom Neurotoxin (Apamin): Iodine Labeling and Characterization of Binding Sites," *Eur. J. Biochem.*, 94:355–364 (1979).
Mourre, C., et al., "Quantitative Autoradiographic Mapping in Rat Brain of the Receptor of Apamin, a Polypeptide Toxin Specific for One Class of CA2+–Dependent K+ Channels," *Brain Res.*, 382:239–249 (1986).
Seagar, M. J., et al., "Molecular Structure of Rat Brain Apamin Receptor: Differential Photoaffinity Labeling of Putative K+ Channel Subunits and Target Size Analysis," *Biochemistry*, 25:4051–4057 (1986).
Seagar, M. J., et al., "Solubilization of the Apamin Receptor Associated with a Calcium–Activated Potasssium Channel From Rat Brain," *J. Neurosci.*, 7:565–570 (1987).
Schmid–Antomarchi, H., et al., "Molecular Properties of the Apamin–binding Component of the CA2+–dependent K+ Channel," *Eur. J. Biochem.*, 142:1–6 (1984).
Wu, K., et al., "Existence of a Ca2+–Dependent K+ Channel in Synaptic Membrane and Postsynaptic Density Fractions Isolated from Canine Cerebral Cortex and Cerebellum, as Determined by Apamin Binding," *Brain Res.*, 360:183–194 (1985).
Seagar, M. J., et al., "Photoaffinity Labeling of Components of the Apamin–sensitive K+ Channel in Neuronal Membranes," *J. Biol. Chem.*, 260:3895–3898 (1985).
Leveque, C., et al., "Polypeptide Components of the Apamin Receptor Associated with a Calcium Activated Potassium Channel," *FEBS Letters*, 275:185–189 (1990).
Marqueze, B., et al., "Photoaffinity Labeling of the K+–Channel Associated Apamin–Binding Molecule in Smooth Muscle, Liver and Heart Membranes," *Eur. J. Biochem.*, 169:295–298 (1987).
Ziai, M. R., et al., "Analysis with Monoclonal Antibodies of the Molecular and Cellular Heterogeneity of Human High Molecular Weight Melanoma Associated Antigen," *Cancer Res.*, 47:2474–2480 (1987).
Ziai, M. R. et al., "An Enzyme–Linked Double Antibody Immunoassay to Measure Muring Immunoglobulins—Its Application to Determine the Specific Activity of Radiolabeled Monoclonal Antibodies," *J. Immunol. Methods*, 82:233–241 (1985).
Hayashibe, K., et al., "A Heterogeneous Double Antibody Enzyme–Linked Immunoassay to Measure β–Galactosidase Fusion Protein,"*J. Immunoassay*, 11:89–95 (1990).
Staros, J. V., et al., "Enhancement by N–Hydroxysulfosuccinimide of Water–Soluble Carbodimide–Mediated Coupling Reactions," *Analyt. Biochem.*, 156:220–222 (1986).

(List continued on next page.)

Primary Examiner—John Ulm
Attorney, Agent, or Firm—Hamilton, Brook, Smith & Reynolds, P.C.

[57] ABSTRACT

The present invention relates to a protein, isolated from a vertebrate tissue sample, of approximately 80 KDa which specifically binds apamin, and to an approximately 55 KDa presumed degradation product of that protein, as well as antibodies which bind to that protein or to the presumed degradation product.

9 Claims, 14 Drawing Sheets

OTHER PUBLICATIONS

Cornett, W. C., et al., "Specificity of Monoclonal Antibodies Reactive with Fusobacterium Nucleatum: Effect of Formalin Fixation," *J. Immunol. Methods,* 84:321–326 (1985).

Lu, et al., "CA2+–activated K+ Channels from Rabbit Kidney Medullary Thick Ascending Limb Cells Expressed in Xenopus Oocytes," *J. Biol. Chem.,* 265:16190–16194 (1990).

Wang, W., "Renal Potassium Channels and Their Regulation," *Annu. Rev. Physiol.,* 54:81–96 (1992).

Atkinson, N. S., et al., "A Component of Calcium–Activated Potassium Channels Encoded by the Drosophila Slo Locus," *Science,* 253:551–555 (1991).

Daniel, S., et al., "Screening for Potassium Channel Modulators by a High Through–Put 86–Rubidium Efflux Assay in a 96–Well Microtiter Plate," *J. Pharmacol Methods,* 25:185–193 (1991).

Messier, C., et al., "Effect of Apamin, a Toxin that Inhibits CA2+–dependent K+ Channels, On Learning and Memory Processes," *Brain Res.,* 551:322–326 (1991).

Fosset, Michel, et al., "The presence in pig brain of an endogenous equivalent of apamin, the bee venom peptide that specifically blocks $Ca^{2+}$–dependent $K^+$ channels", *Proc. Natl. acad. Sci. USA,* 81:7228–7232 (1984).

Lee, Cheng Chi, et al., "Generation of cDNA Probes Directed by Amino Acid Sequence: Cloning of Urate Oxidase", *Science,* 239:1288–1291 (1988).

Sokol, Patricia T., et al., "Cloning of an Apamin Binding Protein of Vascular Smooth Muscle", *Journal of Protein Chemistry,* 13(1):117–128 (1994).

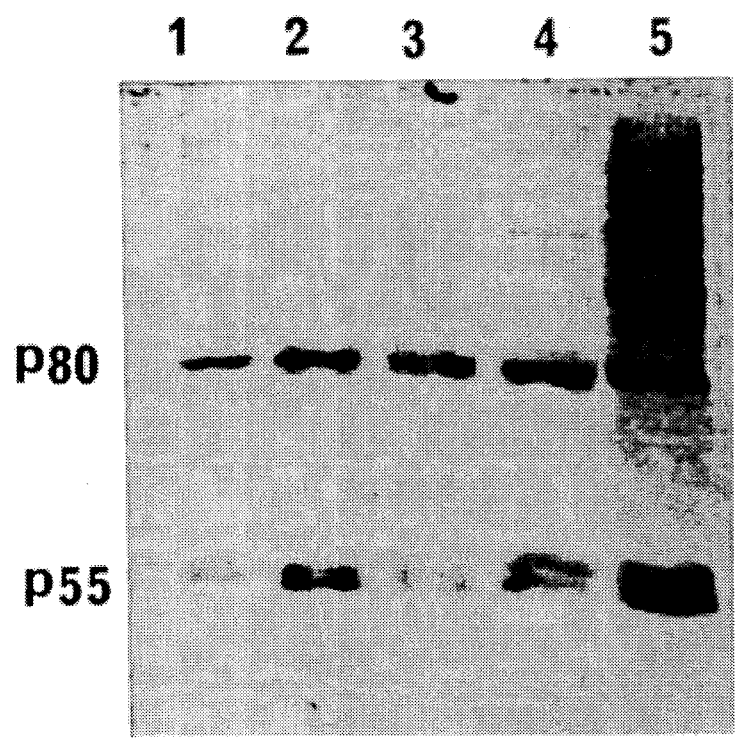

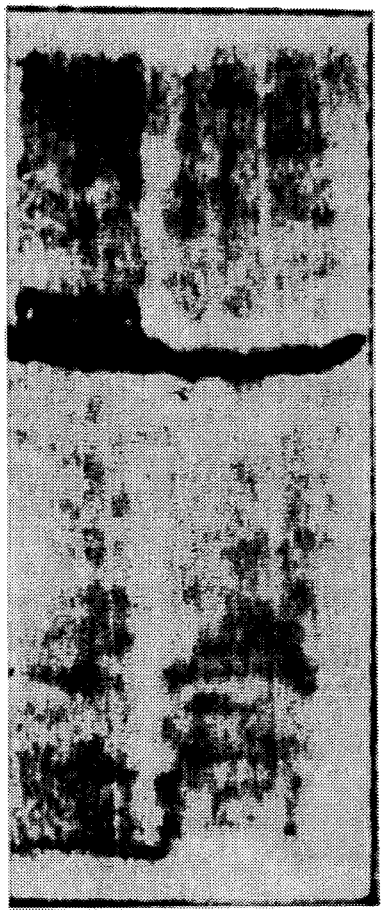

2.1 →

3.0 →
2.1 →

PORCINE APAMIN BINDING PROTEIN/RECEPTOR

RELATED APPLICATIONS

This application is a continuation-in-part of U.S. Ser. No. 07/922,307, filed Jul. 30, 1992, now abandoned, and of U.S. Ser. No. 07/923,095, filed Jul. 30, 1992, now U.S. Pat. No. 5,401,652. The entire teachings of these applications are incorporated herein by reference.

BACKGROUND OF THE INVENTION

Potassium (K) channels are integral membrane proteins of great molecular and functional diversity, present in practically all mammalian cells. These channels are primarily responsible for maintaining a resting membrane potential and are rapidly activated in response to an external depolarizing stimulus, binding of certain ligands, or changes in the intracellular concentration of calcium or ATP. In the excitable cells such as neurons or cardiac myocytes, K-channels determine the duration of the action potential, thus performing a vital function in the central nervous system and the cardiac functions (reviewed in Rudy, B., *Neuroscience* 25:729–749, (1988); Halliwell, J. V., in Cook, N. S. (ed.), *Potassium Channels: Structure, Classification, Function and Therapeutic Potential*, Ellis Horwood Ltd., 348–372, (1990)). The calcium-activated K-channel sub-family consists of at least three discernible ionic currents: a large (BK), an intermediate (IK) and a small (SK) conductive channels (reviewed in Castle, M. A., et al., *TINS*, 12:59–65, (1989); Haylett, B. G. and D. H. Jenkenson, in Cook, N. S. (ed.), *Potassium Channels: Structure, Classification, Function and Therapeutic Potential*, Ellis Horwood Ltd., 70–95, (1990); Latorre, R., et al., *Ann. Rev. Physiol.* 51:385–399, (1989)). These K-channels are activated in response to a rise in the intracellular concentration of calcium $[Ca^{2+}]i$. In addition to calcium $[Ca^{2+}]i$, the BK and IK channels are also sensitive to the changes in the membrane potential, whereas SK-channel has no significant voltage sensitivity.

Functionally, the SK-channel is involved in the after hyperpolarization that follows action potentials in many neurons. These include the sympathetic ganglionic neurons, hippocampal neurons, neurosecretory neurons and spinal motor neurons, as well as the skeletal muscle cells (Rudy, B., *Neuroscience*, 25:729–749, (1988); Latorre, R., et al., *Annu. Rev. Physiol.* 51:385–399, (1989); Pennefather, P. et al., *Proc. Nat'l. Acad. Sci. USA* 82:3040–3044, (1985); Marty, A., *TINS* 12:420–424 (1989); Lancaster, B., et al., *Neurosci.* 11:23–30 (1991); and Strong, P. N., *Pharmac. Ther.* 46:137–162, (1990)). Furthermore, the SK-channel has been suggested to play a major role in the spontaneous, transient outward currents in the tracheal smooth muscle cells (Saunders, H. H., et al., *J. Pharmacol. Exp. Ther.* 257:1114–1119, (1991)), the inhibitory action of the $\propto_1$-adrenoceptors, neurotensin receptor and the P2 of the ATP receptor (Haylett, B. G., et al., in Cook, N. S. (ed), *Potassium Channels: Structure, Classification, Function and Therapeutic Potantial*, 70–95, (1990) and Strong, P. N., *Pharmac. Ther.*, 46:137–162, (1990)).

The neuronal and the skeletal muscle SK-channel is specifically and avidly blocked by a bee venom-derived peptide toxin, apamin (Latorre, R., et al., *Annu. Rev. Physiol.* 51:385–399, (1989); Moczydlowski, E., et al., *J. Membrane Biol.* 105:95–111 (1988); Blatz, A. L., et al., *J. Gen. Physiol.* 84:1–23 (1984); Blatz, A. L. et al., *Nature* 323:718–720 (1986); and Blatz, A. L., et al., *TINS* 10:463–467 (1987)). By all indications, the apamin receptor complex is either identical to, or closely associated with, the SK-channel. Apamin is an 18 amino acid neurotoxic peptide which has a single class of binding sites in the rat brain synaptosomes and rat brain slices with an apparent dissociation constant ($K_d$) of 10–25 pM (Habermann, E., et al., *Eur. J. Biochem.* 94:355–364 (1979); and Mourre, C., et al., *Brain Res.* 382:239–249 (1986)). Apamin is also capable of a temperature dependent and high affinity ($K_d$=30–150 pM) binding to the detergent solubilized brain receptor sites (Seagar, J. J., et al., *Biochemistry* 25:4051–4057 (1986); Seagar, M. J., et al., *Neurosci.* 7:565–570 (1987); Schmid-Antomarchi, H., et al., *Eur. J. Biochem.* 142:1–6 (1984); and Wu, K., et al., *Brain Res.* 360:183–194 (1985)). The reported $B_{max}$ value for the rat brain synaptosomes and brain slices is 10–30 fmol/mg protein (Mourre, C., et al., *Brain Res.* 382:239–249 (1986); Seagar, J. J., et al., *Biochemistry* 25:4051–4057 (1986); and Wu, K., et al., *Brain Res.* 360:183–194 (1985)), while that for the detergent solubilized receptor ranges from 0.45 to 17 fmol/mg protein (Seagar, M. J., et al., *Neurosci.* 7:565–570 (1987); and Schmid-Antomarchi, H., et al., *Eur. J. Biochem.* 142:1–6 (1984)).

The polypeptide components of the apamin receptor have been studied by several groups. Crosslinking experiments using [$^{125}$I]apamin, followed by SDS-PAGE and autoradiography have indicated that the apamin binding proteins of the rat brain synaptosomal membrane consists of two protein species, a major 80–86 KDa protein and, in most reported preparations, a minor 50–59 KDa band (Seagar, J. J., et al., *Biochemistry* 25:4051–4057 (1986); Seagar, M. J., et al., *J. Biol. Chem.* 260:3895–3898 (1985); and Leveque, C., et al., *FEBS Letters* 275:185–189 (1990)). Partial peptide mapping of the two protein bands using an anti-apamin anti-serum has shown that the smaller polypeptide is likely to be a proteolytic fragment of the larger protein and not an additional subunit of the apamin binding protein in the brain. Furthermore, in the plasma membrane of the cultured neurons or astrocytes, there are additional components with the ability to crosslink to [$^{125}$I]apamin. Crosslinking of [$^{125}$I] apamin to the membranes from the rat heart, liver and smooth muscle has also indicated that an 85–87 KDa polypeptide is the major labeled component of the apamin binding complex (Marqueze, B., et al., *Biochem* 169:295–298 (1987)). A second 59 KDa protein was identified in the liver membrane only (Marqueze, B., et al., *Biochem* 169:295–298 (1987)).

The blocking of the small conductance calcium activated potassium channel (sKca) results in prolongation of the action potential, while its activation by an increase in the intracellular calcium concentration accelerates the rate of hyperpolarization, thus shortening the duration of the action potential. In vascular smooth muscle cells (such as those in veins and arteries), activation of sKca results in the hyperpolarization of the smooth muscle membrane, which in turn results in the inhibition of the voltage-gated calcium channels. The inhibition of the latter may then lead to the relaxation of the blood vessels and lowering of the blood pressure. In the heart, modulation of sKca can be a potentially useful means to regulate an arrhythmic heart. In the nervous system, the hypocampus of Alzheimer's patients shows a drastic reduction in apamin density (Vaitukatis, J. L., et al., *Methods in Enzymology* 73:46–52 (1981)). Further, apamin receptor in neurons has been reported to be involved in the process of learning and memory (Messier, C., et al., *Brain Res.* 551:322–326 (1991)). Thus, manipulation of this receptor may also result in improving cognition. Notwithstanding the significant therapeutic potential manipulation of sKca may have, relatively little is known about the identity of the proteins involved in this channel. The present invention now provides key elements in the study of the potassium channel function.

SUMMARY OF THE INVENTION

The present invention relates to a purified and isolated protein which specifically binds apamin. The purified and isolated protein is believed to represent the apamin receptor associated with the SK-channel. Such receptors are associated with calcium activated potassium channels in a variety of animal tissues, such as brain, skeletal, cardiac, vascular smooth muscle, pancreas, kidney and liver tissue.

In one embodiment, the protein of the current invention is approximately 80 KDa, and also yields an approximately 55 KDa presumed degradation product. The isolated protein, or immunogenic or biologically active portions thereof, can be used to generate polyclonal antisera or monoclonal antibodies which are, in turn, useful in study of the structure and function of potassium channels, particularly the small conductance calcium activated potassium channel. By "biologically active" is meant proteins or fragments which are capable of eliciting production of antibodies capable of binding to the receptor, as well as proteins or fragments which are associated with the calcium activated potassium channels (such as BK or IK) but do not necessarily bind apamin. In another embodiment of the current invention, the sequence of the protein is now available; an exemplary sequence of Kcal 1.8, a porcine receptor, is shown as SEQ ID No.:2. The invention also encompasses any amino acid sequence encoded by a nucleotide sequence which hybridizes, under medium or high stringency conditions (as defined in the examples below), with a nucleotide sequence encoding the amino acid sequence of SEQ ID No.:2.

In the heart, modulation of the calcium channel provides a means for regulating an arrhythmic heart; thus, any drug that can open or close this potassium channel is considered a potential anti-arrhythmic agent. Similarly, in vascular smooth muscle cells, such as those in veins and arteries, activation of the potassium channel results in hyperpolarization of the smooth muscle membrane, which in turn results in the inhibition of the voltage-gated calcium channels. The inhibition of the latter will then lead to relaxation of the blood vessels and lowering of blood pressure. The receptor is also associated with cognition functions. Receptor density decreases in Alzheimer's patients, and is involved in the process of learning and memory. Thus, compounds which activate the receptor may be useful in improving impaired cognitive function in Alzheimer's patients, or in enhancing memory and learning capacity. Therefore, a convenient system enabling the detection of compounds that modulate the potassium channel activity has the potential for identifying drugs with tremendous therapeutic utility.

BRIEF DESCRIPTION OF THE FIGURES

FIGS. 3A, 3B and 3C: Western immunoblotting of p80 in the rat brain membranes.

FIG. 3A: The antisera from mouse M1 (lane 1), mouse M2 (lane 2) and a non-immunized mouse (lane 3) are used in immunoblotting of a SDS-solubilized sample of the rat brain membrane proteins. The blots are developed as described below. Arrows indicate the position of two immunoreactive bands, p80 and p55.

FIG. 3B: The anti-p80 monoclonal antibody, D157, is used in immunoblotting of the SDS denatured sample of membranes from bovine brain (lane 1), rat brain (lane 2), rat heart (lane 3), rat kidney (lane 4) and rat liver (lane 5). Arrows indicate the position of p80 and p55.

FIG. 3C: The anti-p80 monoclonal antibody, D157, is used in immunoblotting of the SDS denatured sample of membrane from cultured human melanoma cells A375 (lane 1) and human medulloblastoma cells TE671 (lane 2). The position of p80 is indicated by an arrow.

FIG. 5A: Poly A$^+$-mRNA isolated from adult rat brain (lane 1), or bovine brain (lane 2) or porcine brain (lane 3) are separated on a denaturing agarose gel, blotted onto nitrocellulose, hybridized with $^{32}$p-labelled Kcal 1.6 cDNA and autoradiographed.

FIG. 5B: Poly A$^+$-mRNA isolated from the neonatal rat brain are separated on a denaturing agarose gel, blotted onto nitrocellulose, hybridized with $^{32}$p-labelled Kcal 1.6 cDNA and autoradiographed. The arrows indicate the size (in kilobases) of the two hybridized mRNA bands.

DETAILED DESCRIPTION OF THE INVENTION

The current invention pertains to a protein which specifically binds apamin, and a presumed degradation product; as well as to antibodies which bind the protein or the presumed degradation product.

The following discussion relates to an apamin-binding protein which is isolated from bovine brain. It will be recognized that similar proteins exist in other vertebrates, particularly other mammals, including humans. Additionally, such proteins also occur in other tissues, such as brain, heart, kidney, neuron, melanomas and neuroblastomas as shown below. Isolation of other binding protein subtypes, from alternate species and/or tissues can readily be achieved by the method described. Thus, the invention encompasses any protein with apamin binding specificity, regardless of source.

Figure 1:
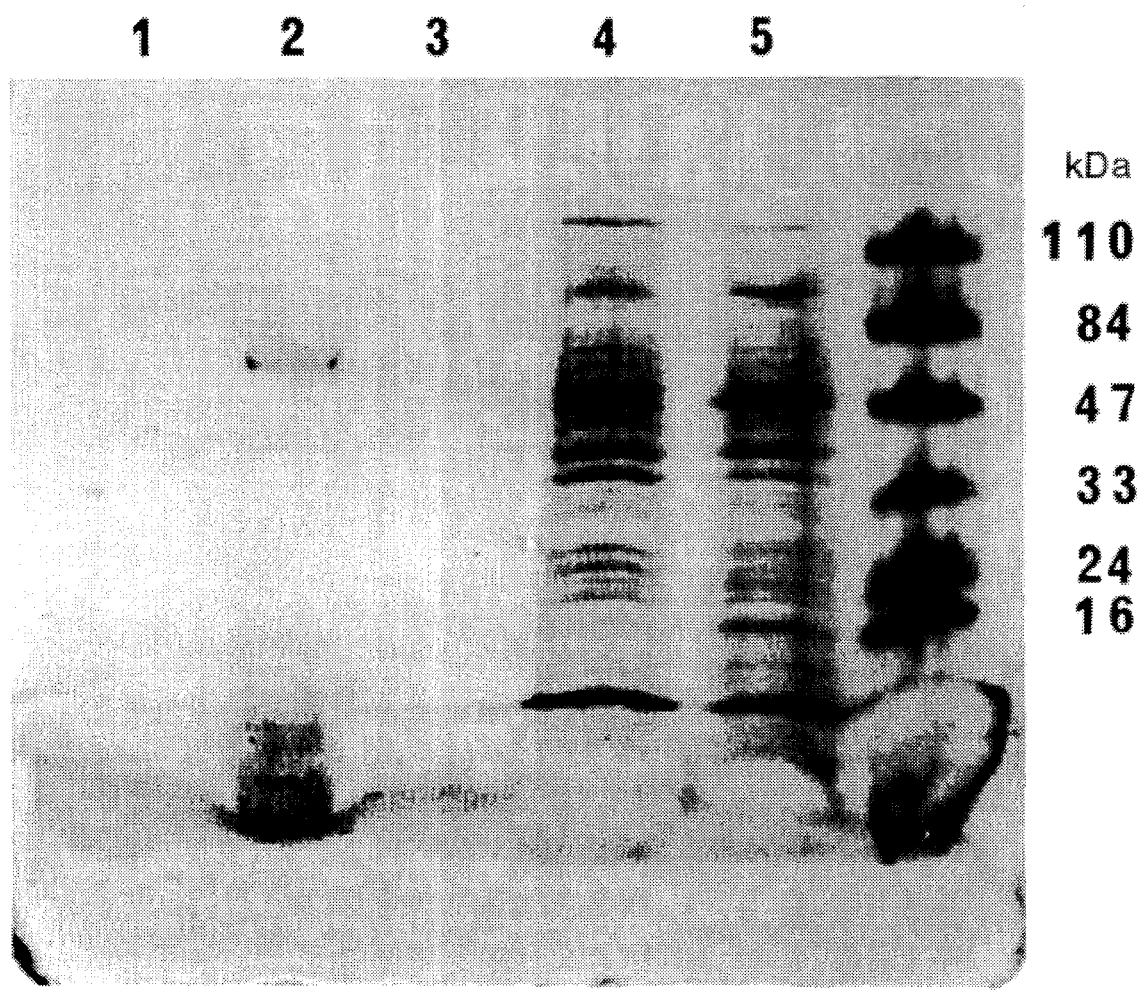
FIG. 1: SDS-PAGE and Coomassie stained analysis of the apamin binding protein, p80 isolated by affinity chromatography on a apamin-Sepharose 4B matrix. The affinity resin, loaded with the CHAPS solubilized bovine brain membranes and extensively washed, is sequentially eluted at 37° C. (lane 1), 42° C. (lane 2) and 55° C. (lane 3). Lanes 4 and 5 show the profile of total CHAPS and SDS solubilized membrane proteins, respectively. The prestained molecular weight standards were phosphorylase B, bovine serum albumin, ovalbumin, carbonic anhydrase, soybean trypsin inhibitor and lysozyme.

In a specific embodiment, an 80 kilodalton (KDa) apamin binding protein is isolated from bovine brain tissue by affinity purification. A crude membrane fraction from brain tissue is solubilized in detergent, and contacted with apamin Sepharose beads to isolate the apamin-binding protein. The affinity matrix is described above. SDS-PAGE separation of the eluate indicates the presence of an 80 KDa protein, hereinafter referred to as p80 (FIG. 1, lane 2).

Figure 2:
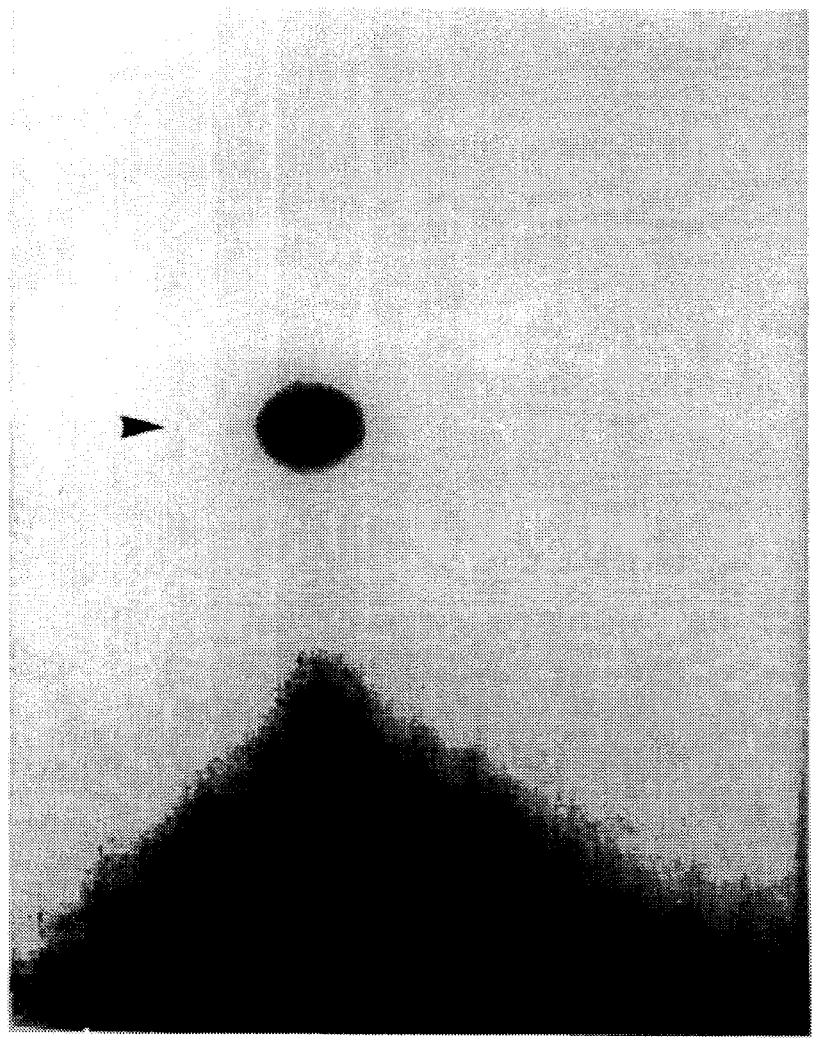
FIG. 2: Cross-linking of [$^{125}$I]apamin to purified p80. Purified p80 is incubated with [$^{125}$I]apamin, without (lane 1) or with (lane 2) an excess of unlabeled apamin. The complex is de-salted, cross-linked, separated by SDS-PAGE and autoradiographed.

The specificity of the interaction between p80 and apamin is tested by a cross-linking experiment. The isolated p80 is incubated with radiolabelled apamin both in the presence and absence of an excess of unlabelled apamin. The labelled apamin-p80 complex is separated from unbound apamin, and treated with the bifunctional cross-linker dimethylsuberimidate (DMS). The cross-linked material, when analyzed by SDS-PAGE and autoradiography, indicates a unique binding between the apamin and p80 (FIG. 2, lane 2). Several repeats of the same experiment with other chemically distinct, bifunctional cross-linking reagents result in the production of a similar band.

The protein thus purified is used to produce both polyclonal and monoclonal sera, as described in the following examples. The polyclonal antisera are used in Western blots of a rat brain synaptosomal preparation. The results indicate the antisera bind to two species, a major 80 KDa protein (p80), and a minor 55 KDa protein (p55). The proteins are not detectable with preimmune sera (See FIGS. 3A–3C).

In order to determine whether the interaction with an 80 KDa and 55 KDa protein indicates that the serum is not monospecific, monoclonal antibodies are prepared and used to analyze the p80/p55 profile in a number of rat tissues. Results with two different monoclonal antibodies show the presence of both p80 and p55 in bovine brain, rat brain, rat heart, rat kidney and rat liver, with rat kidney and liver showing the p55 band as a doublet (FIG. 3B). This indicates an immunological relationship between p80 and p55.

A deglycosylation experiment, together with a partial peptide mapping of the smaller apamin binding protein p55 and p80, has indicated that p55 is likely to be derived from p80 by proteolysis and not by deglycosylation (Leveque, C., et al., *FEBS Letters* 275:185–189 (1990)). Further tests are conducted to determine whether p55 exists in the membrane of freshly isolated cultured cells. To this end, plasma membranes from human melanoma A375 and human medulloblastoma TE671 cells are prepared in the presence of a number of protease inhibitors, separated on SDS-PAGE and analyzed by immunoblotting using monoclonal antibody D157. As shown in FIG. 3C, the antibody detects only one major 80 KDa band in the melanoma cells (lane 1) and TE671 cells (lane 2). A second band slightly larger than p80 is also observed in the melanoma cells (lane 1). In this experiment, no significant amount of p55 is detectable. This observation suggests that p55 is either a proteolytic fragment of p80 generated in vivo or the apamin binding protein complex(es) in the cultured cells is different from that found in the rat and bovine tissues. The latter possibility has been suggested by several groups (Seagar, M. J., et al., *Biochem-istry* 25:4051–4057 (1986); and Seagar, M. J., et al., *J. Neurosci.* 7:565–570 (1987)). However, no direct evidence for this hypothesis has yet been produced and the existence of other sub-units of the apamin receptor complex remains a possibility. These results differ from those obtained by the cross-linking of [$^{125}$I]apamin to its binding proteins in one major respect. The results of the cross-linking experiments indicate that both p80 and p55 bind [$^{125}$I]apamin with an adequate affinity for the covalent bifunctional cross-linking agent to be effective ((Seagar, M. J., et al., *Biochemistry* 25:4051–4057 (1986); Wu, K. et al., *Brain Res.* 360:183–194 (1985); and Leveque, C., et al., *FEBS Letters* 275:185–189 (1990)). The affinity chromatography using the apamin Sepharose 4B column suggests that only p80 binds to the solid phase apamin and no detectable levels of p55 can be found in the eluate (FIG. 1, lane 2). This could be consistent with the hypothesis that p55 is a less mature form of p80, generated by proteolysis and/or post translational processing, and that its affinity for apamin binding may be far lower than that of p80.

Figure 4A:
FIGS. 4A, 4B, 4C, 4D and 4E: Immunocytochemical localization of p80 in rat tissues. The anti-p80 monoclonal antibody, D157, is used to stain a formalinfixed, paraffin embedded section of the rat kidney (FIGS. 4A and 4B). The control section is shown in FIG. 4C. Similarly, a section of the rat brain is either stained with monoclonal antibody D157 (FIG. 4D), or used as a control section (FIG. 4E).
Figure 4B:
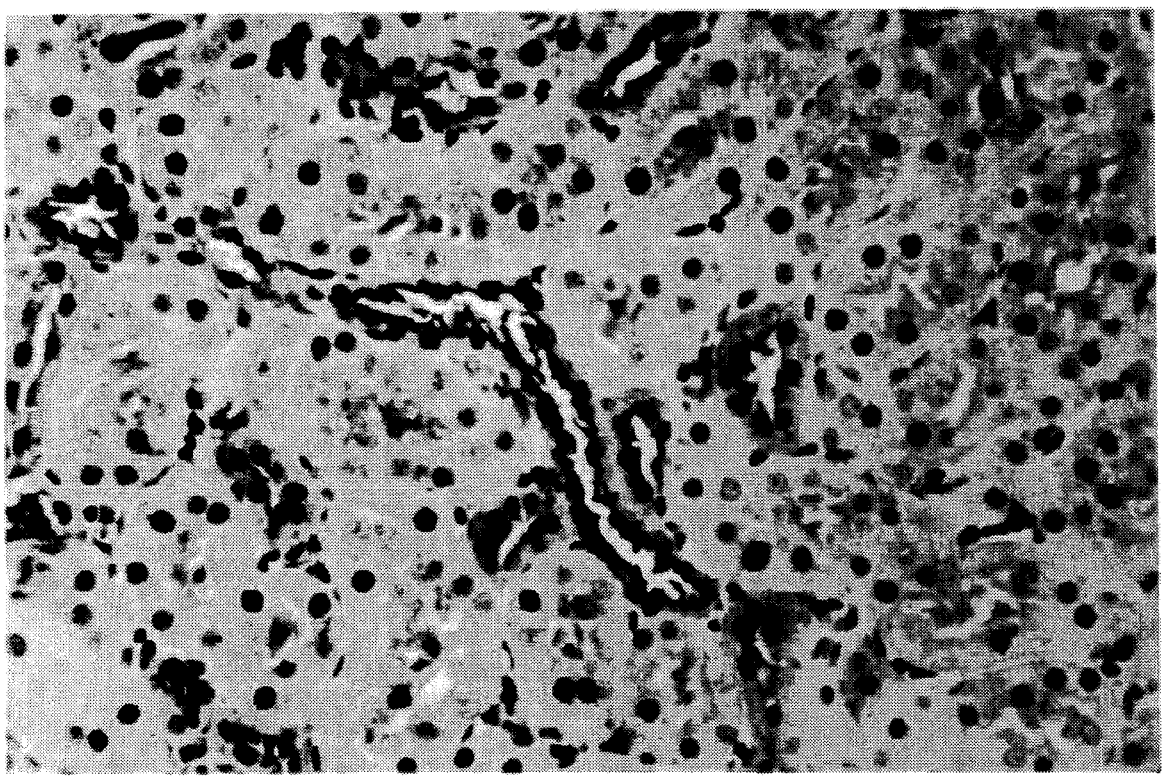
Figure 4C:
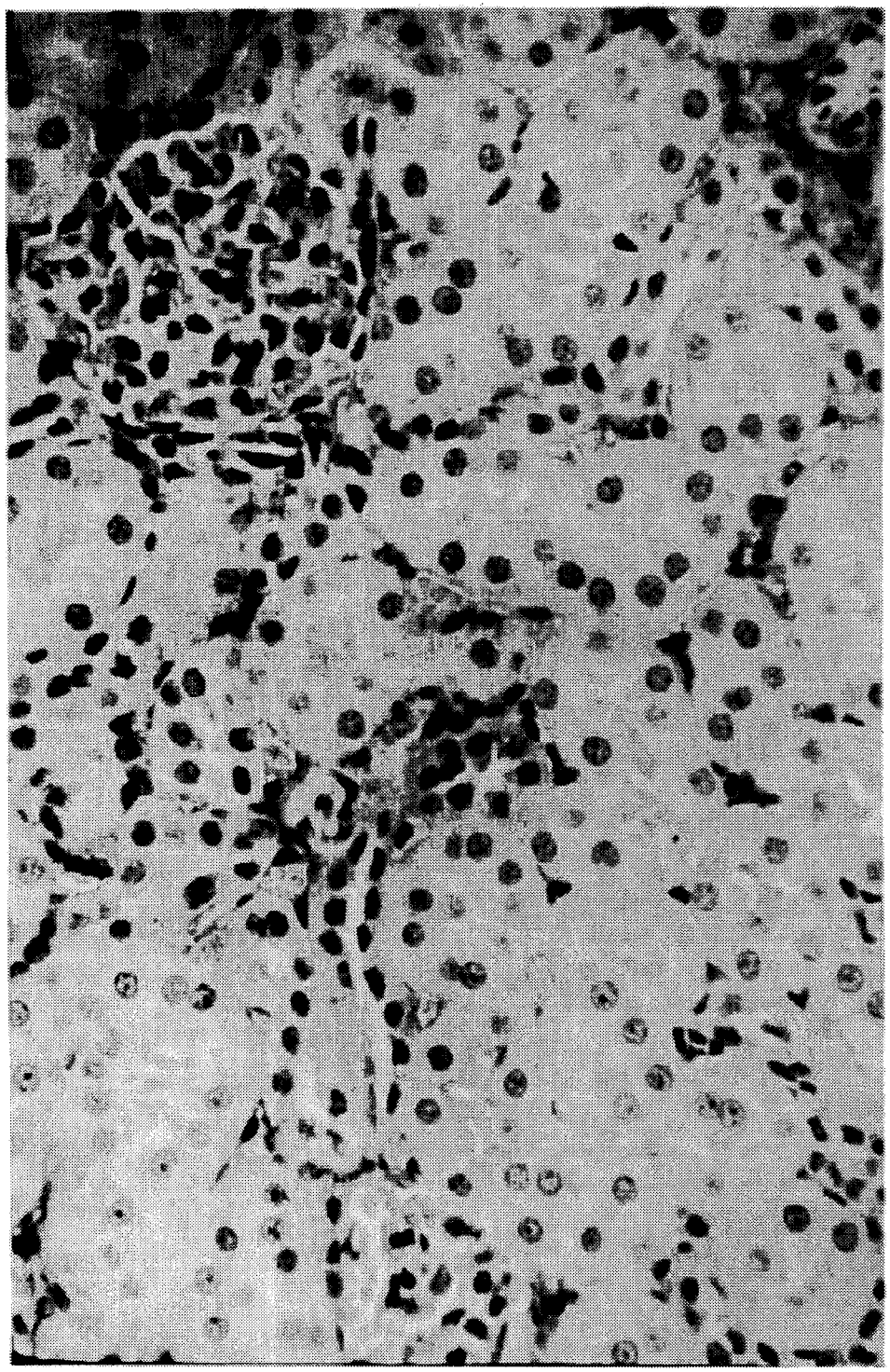

In order to localize p80 and p55 in rat tissue sections, the technique of immunoperoxidase is employed. To this end, formalin fixed paraffin embedded tissue sections are incubated with the ascitic fluid containing the monoclonal antibody D157 at a dilution of 1:10. This monoclonal antibody, in common with a large number of other murine monoclonal antibodies raised against cell surface receptors, is nonreactive or weakly reactive with the formaldehyde fixed tissues (see Cornet, W. C., et al., *J. Immunol,. Methods* 84:321–326 (1985) for an example). Therefore, in this study, it is necessary to use a more concentrated preparation of the antibodies for a consistent staining pattern. As shown in FIGS. 4A and 4B, in the rat kidney, antibody staining is primarily observed in the macula densa and visceral layer of Bowman's capsule (FIG. 4A) and the luminar surfaces of certain distal convoluted tubules (FIG. 4B). No staining of these structures are observed in the control sections (FIG. 4C). At present, the significance of such a restricted localization of p80 in the kidney is unclear. The appearance of the anti-p80 immunoreactivity in certain distal tubules may reflect the developmental and/or functional stages of those distal tubules. A number of reports have identified calcium-activated K-channels in the rabbit renal brush border membranes (Zweifach, A., et al., *Amer. J. Physiol.* 261:F187–F196 (1991)), in the apical membrane of cultured collecting duct epithelium (Laskowski, F. H., et al., *Renal Phys. Biochem.* 13:70–81 (1990)), in cultured medullary thick ascending limb cells (Cornejo, M., et al., *J. Membr. Biol.* 110:49–56 (1989)) and in the luminal membrane of the tubule cells in thick ascending limb of Henle's loop (Klaerke, D. A., et al., *J. Membr. Biol.* 95:105–112 (1987)). In the latter location, the K-channel may be required for maintenance of the lumen positive transepithelial potential and may be important for regulation of NaCl reabsorption (Klaerke, D. A., et al., *J. Membr. Biol.* 95:105–112 (1987)), for K$^+$secretion, and for cell volume regulation (Lu, L., et al., *J. Biol. Chem.* 265:16190–16194 (1990) and Wang, W., et al., *Annu. Rev. Physiol.* 54:81–96 (1992)). In most cases studied, however, the majority of the Ca-activated K-channel involved in the renal function are of the BK type (Wang, W. et al., *Ann. Rev. Psysiol.* 54:81–96 (1992)).

Figure 4D:
Figure 4E:
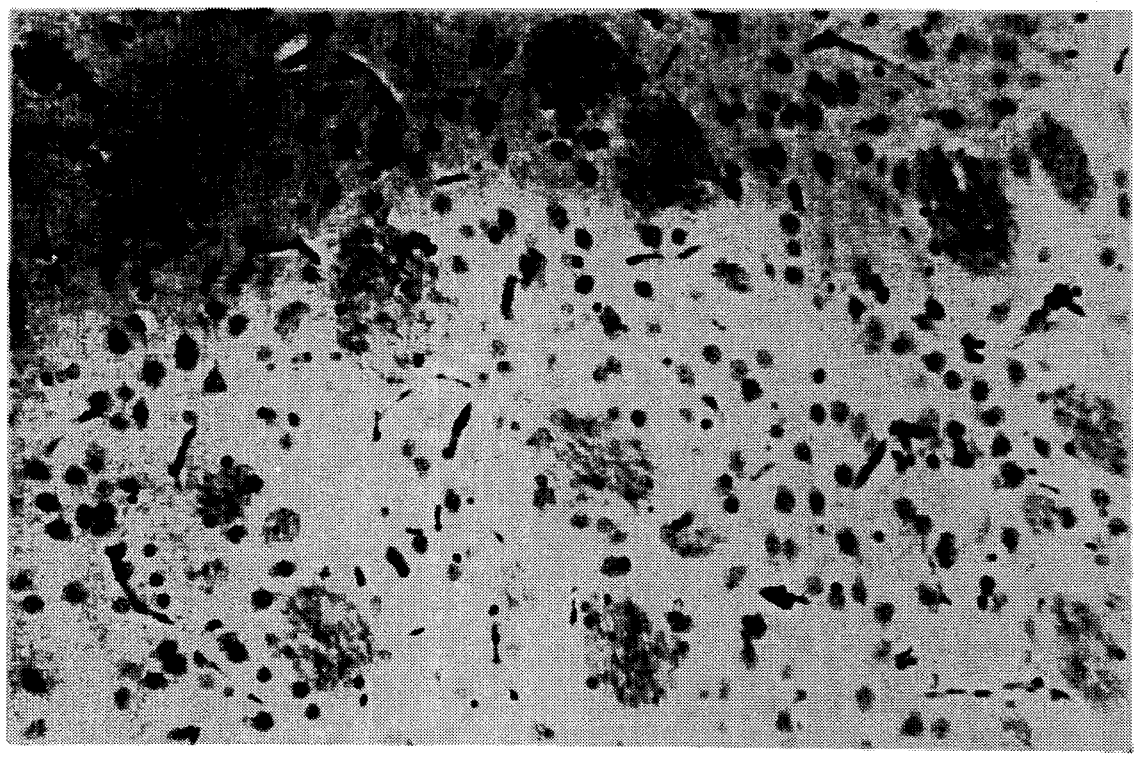

In the rat brain, the monoclonal antibody D157 shows reactivity with the choroid plexus (FIG. 4D) and the hippocampal neurons and naked nerve fibers. These structures are not stained in the control brain sections (FIG. 4E). Using [$^{125}$I]apamin, Mourre et al., (*Brain Res.* 382:239–249 (1986)) studied the distribution of apamin binding sites in various regions of the rat brain. A high density of binding sites was observed in the hippocampal neurons, habenula and olfactory bulb. Another binding study with [$^{125}$I]apamin (Habermann, E. et al., *Eur. J. Biochem.* 94:355–364 (1979)) indicated that the binding sites are primarily enriched in the rat forebrain, brain stem and the cerebellum.

The results described herein are consistent with the interpretation of the 80 KDa protein as an apamin receptor associated with a calcium-activated K$^+$ channel. Further analysis of the predicted amino acid sequence, as described below, confirms a structure having four putative hydrophobic transmembrane domains, and a putative calcium binding domain. The latter shows significant homology to a component of a calcium activated K$^+$ channel in *Drosophila* (Atkinson, N. S. et al., *Science* 253:551–555 (1991)).

Those skilled in the art will recognize that, although the exemplified apamin binding protein is derived from brain, the invention is not limited to a protein derived from this source. As the immunochemical data presented herein demonstrates, homologous proteins exist in other tissues and other species, and are isolatable by the methods described herein. The invention thus also encompasses those apamin binding proteins produced in other tissues, in particular those expressed in heart, vascular smooth muscle, neurons, kidneys, pancreas, human melanomas and neuroblastomas.

As noted above, the isolated protein, which on SDS-PAGE is about 90–95% pure, is useful for the generation of monoclonal and polyclonal antibodies which are in turn useful in screening DNA libraries for production of apamin binding protein cDNA homologues. Since the apamin receptor is also expressed in melanomas and neuroblastomas, the monoclonal antibodies are useful in tumor imaging when conjugated to an appropriate imaging agent, or in tumor therapy, when conjugated to an appropriate cytotoxic agent. Also, the monoclonal antibodies are useful for affinity purification of apamin receptors from other tissues. For example, the antibody can be immobilized in the same manner as apamin on EAH-Sepharose, as described in the examples below, and used in the affinity chromatography in substantially the same manner. Alternately, the antibody can be immobilized on cyanogen bromide activated sepharose, Affigel®, or any other appropriate affinity matrix. Such matrices are well known to those skilled in the art.

The isolated receptor protein is also useful in assays for identifying compounds which may act as analogs of apamin, i.e., which can modulate the activity of the apamin receptor. For example, the receptor protein can be immobilized by any means which does not interfere with apamin binding activity. The immobilized receptor is then contacted with a specific compound or mixture and the ability to compete with radiolabelled apamin for binding to the receptor is evaluated. Also, p80 or other isolated apamin binding protein is useful for developing an immunoassay to measure the level of apamin receptor in patients' serum for diagnosis of neural degeneration. Variations of this method will be apparent to those skilled in the art. The above embodiments of the invention are further described in examples 1–6.

A full-length apamin binding protein nucleic acid sequence, encoding the protein described above, is isolated from a porcine vascular smooth muscle (aorta) expression cDNA library in a λ-ZAP vector. The library is screened with polyclonal sera raised against a bovine brain apamin receptor. Screening of about 2 million plaque forming units yields four positive plaques which are rescreened and plaque purified.

Figure 5A:
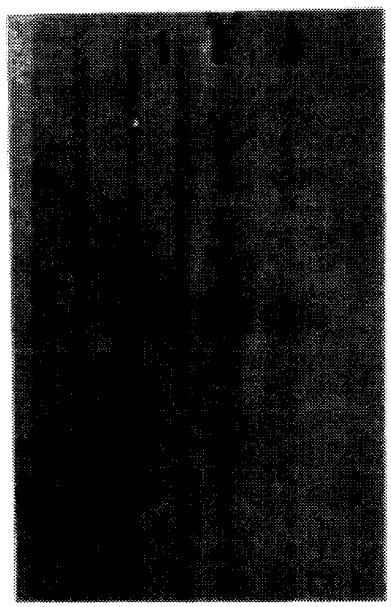
FIGS. 5A and 5B: Northern blotting of the mRNA encoding the apamin receptor.
Figure 5B:
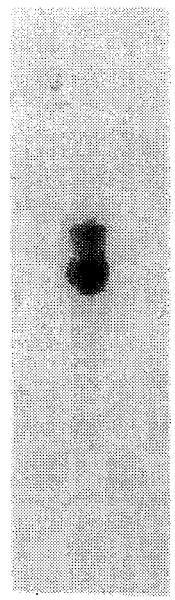

The λZAP is transformed into "pBluescript" plasmid by standard techniques; the DNA is then digested with the restriction endonucleases EcoRI and XhoI to release the cDNA inserts, and analyzed by agarose gel electrophoresis. One 1.6 Kb cDNA clone (designated Kcal 1.6) is selected for Northern hybridization, genomic Southern blotting and DNA sequencing. As shown in FIG. 5A, the cDNA Kcal 1.6 detects a single band of approximately 2.1 Kb in the adult rat brain mRNA (lane 1), bovine brain mRNA (lane 2) and porcine brain mRNA (lane 3). The probe, however, reveals two mRNA bands of 2.1 and 3.0 Kb in size in the Northern blot of mRNA from neonatal rat brain (FIG. 5B). These results suggest that in the neonatal rat brain, there are two distinct mRNA species which hybridize to Kcal 1.6, possibly arising by the alternate splicing of mRNA.

Figure 6:
FIG. 6: Genomic Southern hybridization analysis of Kcal 1.6. EcI cut-genomic DNA from human (lane 1), monkey (lane 2), rat (lane 3), mouse (lane 4), dog (lane 5), cow (lane 6), rabbit (lane 7), chicken (lane 8) and yeast (lane 9) are hybridized with $^{32}$p-labelled Kcal 1.6 cDNA and autoradiographed.

Next, an EcoRI cut-genomic southern blot probed with Kcal 1.6 cDNA. As shown in FIG. 6, after repeated washing of the blot at high stringency, the Kcal 1.6 probe detects a single 14 Kb band in human (lane 1) and in monkey (lane 2). However, there are variable patterns of hybridization in the rat (lane 3), mouse (lane 4), canine (lane 5), bovine (lane 6), rabbit (lane 7) and chicken (lane 8). There is no detectable hybridization with the yeast DNA (lane 9). This experiment indicates that there are significant sequence homologies among the genes encoding p80 in various species. Furthermore, the gene(s) encoding p80 in human and monkey are probably more similar than those in other species.

Figure 7:
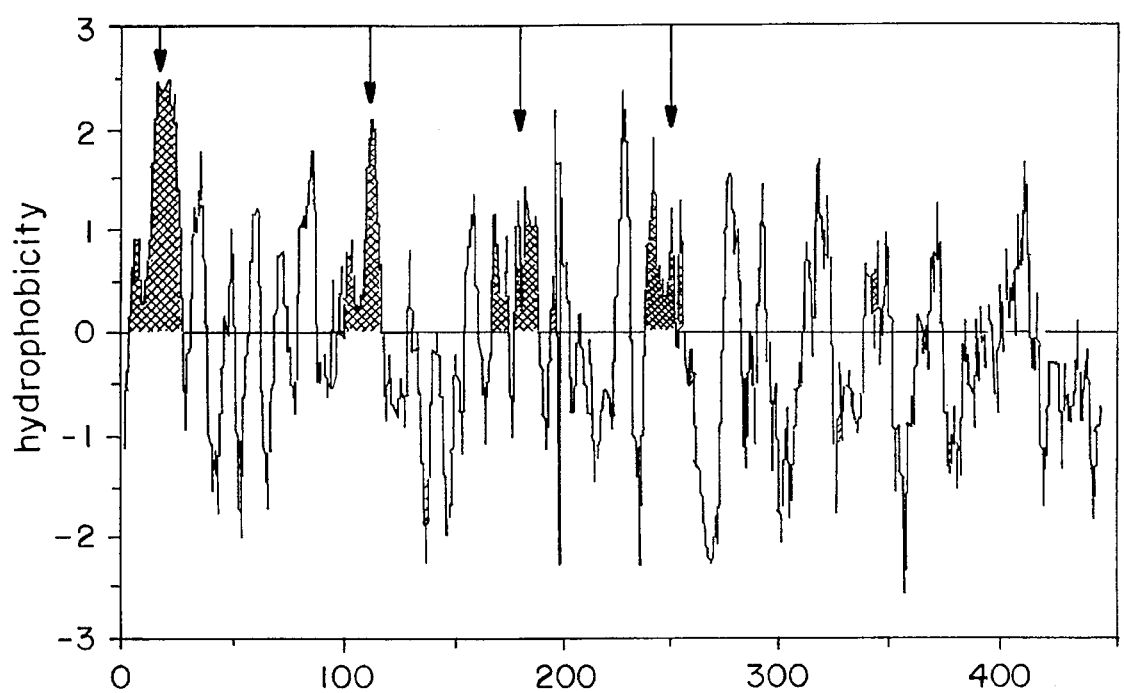
FIG. 7: The hydropathy plot for the protein encoded by Kcal-1.8 cDNA. The four putative but strong hydrophobic domains are indicated by arrows.

Kcal 1.6 cDNA is then sequenced. The nucleotide sequence obtained indicates that the clone is not of full length and lacks the initiation methionine residue. To obtain a full-length clone, Kcal 1.6 is used as a probe and the original porcine aorta cDNA library is screened, and positive clones analyzed by restriction mapping and electrophoresis for relatedness and insert size. One cDNA clone (designated Kcal 1.8), which appears to be slightly longer than Kcal 1.6, is selected and sequenced by a Taq polymerase sequencing technique. When the nucleotide sequence (SEQ ID No.:1) is translated in frame, the cDNA Kcal 1.8 encodes a protein (SEQ ID No.:2) of 437 amino acids, with an initiation methionine and a stop site. Hydrophobicity analysis (FIG. 7) of the sequence indicates the presence of four strongly hydrophobic putative transmembrane domains (TMDI-4), a short amino terminus and a long carboxyl terminus. The sequence has some interesting features. It contains a strong "EF-Hand" consensus sequence. The EF-Hand consensus sequence is present in virtually all calcium binding protein members of calmodulin and troponin C families. In fact, the EF-Hand motif in Kcal 1.8 almost perfectly matches that of calmodulin, as well as a recently cloned component of *Drosophila* calcium activated K-channel, "Slo" (Ohandra, M. et al., *Toxicol. Pathol.* 19:164–167 (1991)). In addition, the sequence flanking the putative "EF-Hand" motif of Kcal 1.8 has significant homology with a number of known calcium binding proteins including troponin C, myosin, calreticulin, PEP-19, and several others. Since the small conductance calcium-activated potassium channel (sKca) must have a calcium binding site, it gives further support to the belief that Kcal 1.8 indeed encodes sKca. If the "EF-Hand" motif is in fact a calcium binding site of Kcal 1.8 protein, it places the "EF-Hand" motif on the cytoplasmic side of the membrane. The amino acid sequence of Kcal 1.8 also contains one protein kinase C site, and one tyrosine kinase phosphorylation site. In addition, a "leucine zipper" motif can be identified in the C-terminal portion of the protein. At present, the significance, if any, of this motif in Kcal 1.8 is unclear. However, the presence of these putative phosphorylation sites, together with the "EF-Hand" motif are likely to place both N- and C-termini of the protein in the cytoplasmic side of the plasma membrane.

To further confirm Kcal 1.8's identity as an apamin receptor, Kcal cDNA is introduced into a stable mammalian expression vector, pRC/CMV, which is used to transfect CV-1 cells (African green monkey kidney). Cells stably expressing the Kcal 1.8 gene product are selected and are contacted with radiolabelled apamin, in the presence or absence of unlabelled apamin. A number of transfectants show enhanced binding of radiolabelled apamin, thereby adding further confirmation of Kcal 1.8's identity.

The foregoing discussion, and the sequences provided in SEQ ID No.:1 and No.:2, relate to a porcine smooth muscle apamin receptor. However, it will be understood that the invention encompasses more than the specific exemplary sequences. Modifications to the sequence, such as deletions, insertions, or substitutions in the sequence which produce silent changes in the resulting protein molecule are also contemplated. For example, alteration in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. It may also be desirable to eliminate one or more of the cysteines present in the sequence, as the presence of cysteines may result in the undesirable formation of multimers when the protein is produced recombinantly, thereby complicating the purification and crystallization processes. In some cases, it may in fact be desirable to make mutants of the sequence in order to study the effect of alteration on the biological activity of the protein. Each of the proposed modifications is well within the routine skill in the art, as is determination of retention of biological activity of the encoded products.

The invention also encompasses homologous proteins obtained from other species and other tissues. As has already been demonstrated above, the nucleic acid sequence encoding the protein depicted in SEQ ID No.:2 hybridizes, under relatively stringent conditions, with nucleic acid fragments present in a number of other species, including human, thus demonstrating the ability to isolate other non-porcine sequences and other proteins. Moreover, apamin receptors from tissue types other than vascular smooth muscle are also known to exist. Brain, skeletal muscle, and liver, in addition to vascular smooth muscle, have been repeatedly demonstrated to express a single class of binding site (Haylett, B. G., et al., *Potassium Channels; Structure, Classification, Function and Therapeutic Potential*, 70–95 (1990); Habermann, E. et al., *Eur. J. Biochem.* 94:355–364 (1979); Mourre, C., et al., *Brain Res.* 382:239–249 (1986); (Seagar, J. J., et al., *Biochemistry* 25:4051–4057 (1986); Seagar, M. J., et al., *J. Neurosci.* 7:565–570 (1987); Schmid-Antomarchi, H., et al., *Eur. J. Biochem.* 142:1–6 (1984); and Wu, K., et al., *Brain Res.* 360:183–194 (1985)). On the other hand, cardiac tissue seems to exhibit a heterogeneous population of target sites. The sequence disclosed in SEQ ID No.:1 can thus be used as a probe to isolate the corresponding receptors from other species and tissues. Alternate receptor types are isolatable as follows. cDNA libraries prepared from mRNA from the specific tissue type of interest are probed with radiolabelled Kcal 1.8 cDNA and washed under medium stringency (e.g., 1×SSC, 0.1% SDS, 55° C.). Plaques which appear positive are rescreened to verify authenticity. The positive plaques are then used in plasmid rescue according to techniques known in the art. Rescued plasmids are purified, cut with appropriate restriction enzymes, and analyzed in an agarose gel stained with ethidium bromide. The second gel is transferred to an nitrocellulose filter, probed with labelled Kcal 1.8, washed sequentially under a medium, then high stringency (0.1×SSC, 0.1% SDS, at 65° C.) wash and exposed to X-ray film. Those inserts which strongly hybridize to Kcal 1.8 under high stringency conditions represent likely receptor cDNA candidates. Further confirmation of the identity of these putative receptors can be accomplished according to the protocols described in the following examples, or in accordance with routine techniques known in the art. Thus, the invention encompasses not only the amino acid sequence depicted in SEQ ID No.:2, but also amino acid sequences encoded by nucleotide sequences which hybridize, under medium or high stringency conditions, with nucleotide sequence (SEQ ID No.:1) encoding the amino acid sequence (SEQ ID No.:2) of as well as the biologically active proteins or fragments encoded thereby.

The ability of any given isolated DNA sequence to yield a functional apamin receptor is determinable by a simple apamin binding assay. Transfected cells are prepared as previously described (Daniel, S., et al., *J. Pharmacol. Methods* 25:185–193 (1991)). Binding assays are performed by a standard procedure (Mourre, C., et al., *Brain Res.* 382:239–249 (1986)), and values for maximum binding of ligand to receptor (Bmax) and dissociation constant ($K_d$) for each cell line is calculated.

Further evaluation of the measurement of potassium channel activity in cultured transfectant cells is accomplished by $^{86}Rb$ efflux assay (Vaitukatis, J. L., *Methods in Enzmoymology* 73:46–52 (1981), incorporated herein by reference). Briefly, stably transfected cells are loaded overnight with $^{86}Rb$ in microtiter plates, the medium is then discarded and adherent cells washed three times to remove isotope. Cells are then incubated for 30 minutes at 37° C. with an isotonic buffer containing 20 mM $CaCl_2$ and 100 μM calcium ionophore A23187. The supernatants from wells are recovered and counted. The cell layer is solubilized in Triton X-100 and also counted, and the percent efflux of $^{86}Rb$ calculated as described. The experiment is carried out in the presence or absence of 1 mM apamin (an sKca blocker) or 1 μM charybdotoxin (a BKca blocker), and control experiments carried out in parallel with cells being incubated with buffer, but without added ionophore. The percent efflux in transfectants harboring cloned DNA mock transfectants, and wild-type CV-I cells (to measure endogenous efflux) are compared. Such assays are also useful in determining the effect of structural change in the channel in its function, and also to evaluate functional differences between different receptor subtypes. This assay is useful both in confirming activity of a putative receptor/channel as well as confirming the effects.

DEPOSIT OF BIOLOGICAL MATERIALS

The following biological materials were deposited with the American Type Culture Collection, 12301 Parklawn Drive, Rockville, Md., on Jun. 15, 1992, and given the Accession Numbers indicated:

| Material | Accession No. |
| --- | --- |
| E. coli containing pBluescript plasmid containing Kcal 1.8 | ATCC 69017 |

The above embodiments of the current invention are further illustrated by examples 7–9.

EXAMPLES

1. Tissue Homogenization and Plasma Membrane Solubilization

Freshly frozen bovine brain (300 g) is homogenized for two minutes in a Waring blender in five volumes of buffer "H"; tris-HCl (20 mM), KCl (3.0 mM), phenylmethylsulfonylfluoride, PSMF (0.1 mM), EDTA (0.1 mM), leupeptin (2.0 ug/ml), pH 7.0 at 4° C. The homogenate is centrifuged at 500×g for 45 minutes at 4° C. The supernatant is discharged, the crude membrane pellet is resuspended in 100 ml of buffer "H" containing 15% v/v glycerol and stored in 10 ml aliquots at −80° C. until used.

In order to determine which detergent permits the binding of the apamin binding proteins to this affinity matrix, a number of ionic and non-ionic detergents are tested. The maximum degree of binding is observed when 1% w/v CHAPS or Lubrol-PX is used to solubilize the synaptosomes. A 1% v/v preparation of Triton X-I00, Nonidet P-40, or SDS does not permit an efficient binding of the solid phase apamin to its binding proteins. In view of the dialysable nature of CHAPS, it is selected as the solubilizing detergent.

Frozen aliquots (50 ml) are rapidly thawed in a 37° C. water bath and gently mixed with an equal volume of ice-cold buffer "S": tris-HCl (40 mM), KCl (10 mM), CaCl2 (0.1 mM), $MgCl_2$(0.1 mM) and CHAPS (2% w/v), pH 7.4. The mixture is shaken gently at 4° C. for 30 minutes, centrifuged at 30,000×g for 30 minutes at 4° and the clear supernatant is collected.

2. Preparation of Apamin-Sepharose 4B Affinity Matrix

EAH-Sepharose 4B (20 ml, Pharmacia, LKB, Piscataway, N.J.) is washed with 20 mM MOPS (4-morpholine propane sulfonic acid), pH 7.0 as described by the manufacturer. The beads are resuspended in 5.0 ml of 20 mM, MOPS, pH 7.0 containing 0.5 µmol of apamin and supplemented with 1.0 pmol of [$^{125}$I]apamin as a tracer. Solid 1-ethyl-3-(3-dimethylaminopropyl) carbodiimide hydrochloride (EDC, Pierce Chemical Co., Rockford, Ill.) and N-hydroxysulfosuccinimide (sulfo- NHS, Pierce Chemical Co., Rockford, Ill.) are added to the suspension at a final concentration of 100 mM and 5.0 mM, respectively. The suspension is mixed for 24 hours at 4° C., the beads are washed three times with 10 volumes of 20 mM, MOPS, pH 7.0 containing 0.5M NaCl and an aliquot is counted in a gamma counter. The coupling efficiency is calculated based on the coupling of the tracer apamin. The method results in the coupling of 33 nmole of apamin per milliliter of the EAH Sepharose beads.

3. Purification of Apamin Binding Proteins

The CHAPS solubilized membrane (50 ml) is pre-cleared twice, each for 30 minutes at 4° C. by incubation and shaking with 1.0 ml of EAH-Sepharose beads (packed volume). The beads are removed by centrifugation at 500×g for 5 minutes and the supernatants are added to 1.0 ml of apamin-Sepharose beads (packed volume). The suspension is incubated at 4° C. for 4 hours with constant shaking, centrifuged at 500×g for 5 minutes at 4° and the supernatant discarded. The beads are washed four times at 4° C., each time by gently resuspending in 50 ml of ice-cold buffer "S" diluted with an equal volume of distilled water, followed by centrifugation as above. In order to elute the apamin binding proteins, the final pellet of beads is resuspended in 10 ml of tris-HCl (10 mM), KCl (10 mM), pH 7.4 (binding buffer, "B") containing CHAPS (0.1% w/v) and placed in a 42° C. water bath for 15 minutes with constant shaking. As shown in FIG. 1, incubation of the beads in elution buffer for 15 minutes at 37° C. does not lead to elution, but the rapid shift to 42° C. results in elution of an 80 KD protein, p80 (FIG. 1, lane 1). Further incubation at 55° C. does not result in detectable elution of other proteins (FIG. 3, lane 3). The beads are removed by centrifugation at 1500×g for 10 minutes and the supernatant is collected. This procedure is repeated once more and the supernatant is collected. The supernatants containing the eluted apamin binding protein are either used immediately for binding studies, or concentrated by negative pressure dialysis at 4° C. and stored at −20° C.

4. Cross-Linking of [$^{125}$I]Apamin Binding Proteins

The specificity of the interaction between p80 and apamin is tested by a cross-linking experiment. The protein fraction (100 ng) eluted from the apamin affinity matrix is incubated on ice for 1 hour with 1.0 pmol of [$^{125}$I]apamin (2200 Ci/mmol, New England Nuclear, Boston, Mass.), in a final volume of 100 µl of buffer "B", with or without the inclusion of unlabelled apamin (final concentration of 1.0 µM). This is an essential precaution since the apamin binding ability of p80 is lost within 2 hours of elution from the affinity matrix. This observation of instability of detergent solubilized apamin binding proteins is in agreement with the findings of Schmid-Antomarchi et al. (Eur. J. Biochem. 142:1–6 (1984)). The [$^{125}$I]apamin-P80 complex is then separated from unbound [$^{125}$I]apamin by loading at 4° C. on a G-50 Sephadex "Quickspin" column (Boehringer Mannheim, Indianapolis, Ind.) pre-equilibrated with sodium borate (50 mM) buffer, pH 8.0. To the collected void fraction (100 µl) is added 10 µl of a 10 mM stock in dimethylsulfoxide of dimethylsuberimidate (DMS, Pierce Chemical Co., Rockford, Ill.). The mixture is incubated on ice for 1 hour, quenched by addition of ammonium acetate (100 mM final), lyophilized, counted in a gamma counter and analyzed by SDS-PAGE using a Phast System (LKB-Pharmacia, Piscataway, N.J.) or by using conventional techniques. Gels are fixed and stained with 0.1% Phase Gel-Blue (LKB-Pharmacia), 20% acetic acid and 20% v/v methanol and destained in 5% v/v acetic acid and 25% v/v methanol in distilled water. Autoradiography is carried out at −80° C. using X-OMAT-AR films and one intensifying screen.

As shown in FIG. 2 (lane 1), [$^{125}$I]apamin is uniquely cross-linked to p80, while the excess and uncross-linked [$^{125}$I]apamin appears at the dye front. The interaction is considered specific, since the inclusion of the excess unlabeled apamin completely abrogates the cross-linking of [$^{125}$I]apamin to p80 (FIG. 2, lane 2). In addition to DMS, the same experiment is repeated with four other, chemically distinct, bifunctional cross-linking reagents. Each time, the cross-linked protein band on the autoradiogram is superimposable to the p80 band in the Coomassie stained gel.

5. Preparation of Monoclonal Antibodies

Female balb/c mice (8–10 weeks old) are immunized with the affinity purified apamin binding protein as prepared above. Mice are immunized with a total of 2.0 µg of protein emulsified in complete Freund's adjuvant by one intraperitoneal and six equal subcutaneous injections. Animals are rested for 30 days, following which they are immunized as before, but with incomplete Freund's adjuvant. The animals are boosted every two weeks by a single intraperitoneal injection of 100 ng of the protein emulsified in incomplete Freund's adjuvant. Fourteen days after the fourth immunization, mice are test bled from the orbital sinus and polyclonal sera collected and tested for reaction with affinity purified receptor. A final immunization is then given, and three days later, the animals are sacrificed and the spleens removed.

Splenocytes from animals producing positive polyclonal sera are fused with the murine myeloma cell line X63-Ag 8.653. Hybridomas are selected and subcloned by standard procedures (Ausuber, F. M., et al., (eds.), *Current Protocols In Molecular Biology II:* 11.3–11.16, Wiley Interscience (1989)). Hybridoma supernatants are screened in a solid phase ELISA using purified apamin binding protein as the target antigen as previously described (Zia, M. R., et al., *Immunol. Methods* 82:233–241 (1985) and Hayashibe, K., et al., *J. Immunoassay* 11:89–95 (1990)), as well as in an apamin binding neutralization assay. In this assay, bovine brain plasma membranes are incubated with the diluted hybridoma for 1 hour at 4° C. The binding assay is carried out at 4° C. in buffer "B": tris-HCl (20 mM), KCl (5.0 mM), BSA (0.1% w/v), PMSF (0.1 mM), SCH 32,615 (0.1 mM), pH 7.4. A binding assay for receptor is performed in a total volume of 200 μl; synaptosomal membranes (50 μl), [$^{125}$I] apamin (0.1 pmol in 20μ), hybridoma supernatants (50 μl) and buffer B (to 200 μl). The mixture is incubated at 4° C. for 2 hours. The assay mixtures are filtered on a glass fiber filter GF/C. The membranes are washed with buffer B and filters are counted in a Pharmacia-LKB gamma counter. Ascitic fluids are produced and collected in balb/c mice pretreated with pristane using standard protocols. The foregoing procedure yields at least two positive hybridomas, producing monoclonal antibodies identified herein as A114 and D157. Both antibodies are of the IgG1 subtype, with no detectable contamination with any other IgG or IgM isotypes.

6. Distribution of p80

Figure 3A:
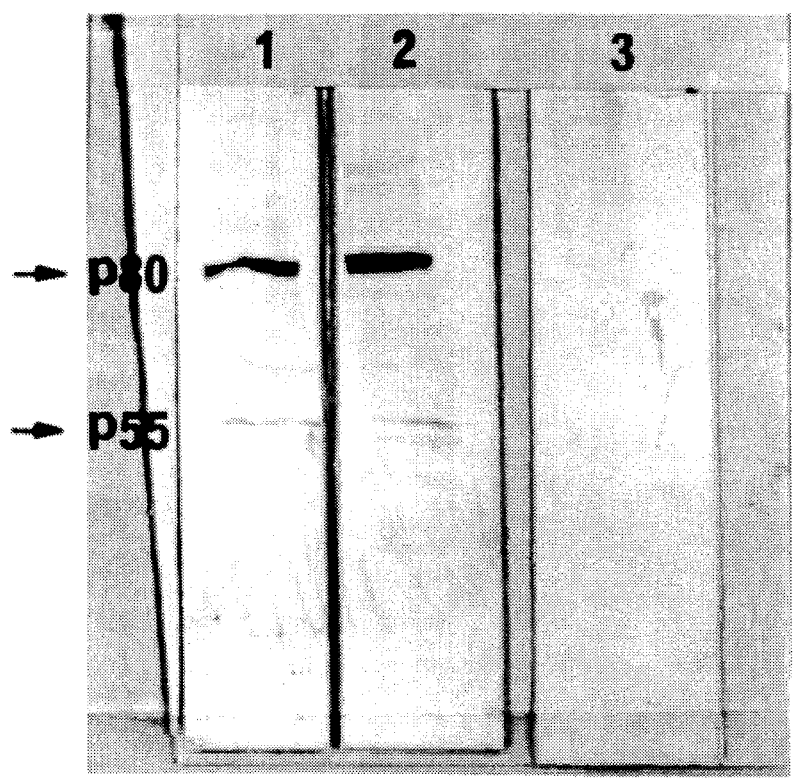

Polyclonal and monoclonal antibodies are generated to p80 to enable characterization of p80 Western blotting and to perform immunocytochemistry in tissue sections. The anti-p80 polyclonal antisera from two immunized mice are used in Western blotting (standard techniques, detected by Vectastain ABC Kit, Vector Laboratories, Burlingame, Calif.) using a rat brain synaptosomal preparation separated on SDS-PAGE, as described above, and transferred onto nitrocellulose. As shown in FIG. 3(A), the antisera from two immunized mice react with a major 80 KDa protein (p80) and a minor 55 KDa protein (p55) bands (lanes 1 and 2), neither of which is detected when a pre-immune serum is used (lane 3). The presence of an immunochemical reactivity towards a p55 protein suggests two possibilities. Either the murine antiserum is not mono-specific, or the p80 and p55 are immunologically related. To resolve this question, using the monoclonal antibody D157, the p80/p55 profile is analyzed in several rat tissues. Preparation of the formalin fixed, paraffin embedded sections from rat tissues, application of primary antibodies, detection by the avidin-horseradish peroxidase (Dako), counter shaking by hematoxylin and mounting are performed by standard procedures and as described (Ohandra, M. et al., *Toxicol. Pathol.* 19:164–167 (1991)). As shown in FIG. 3(B), the monoclonal antibody D157, diluted 1:10,000, reacts strongly with p80 and p55 in membranes isolated from bovine brain (lane 1), rat brain (lane 2), rat heart (lane 3), rat kidney (lane 4) and rat liver (lane 5). In the rat kidney and liver, the p55 band appears as a doublet (FIG. 3B, lanes 4 and 5). Identical results are obtained with the other anti-p80 monoclonal antibody, A114 at 1:10,000 dilution. The immunoreactivity of these monoclonal antibodies with p80 and p55 indicates that the two proteins must be immunologically related. The presence of a 55 KDa protein, in addition to a 80 KDa apamin binding protein, has been documented by several groups (Seagar, M. J., et al., *Biochemistry* 25:4051–4057 (1986), Seagar, M. J., et al., *J. Biol. Chem.* 260:3895–3898 (1985), Leveque, C., et al., *FEBS Letters* 275:185–189 (1990) and Marqueze, B., et al., *Eur. J. Biochem* 169:295–298 (1987)).

7. Screening Expression Library

A porcine aorta expression cDNA library in λ-Uni ZAP λR (Stratagene, La Jolla, Calif.) is probed with a 1:1000 dilution of a murine anti-apamin binding protein polyclonal antiserum (M2) using the Vectastain ABC kit (Vector Laboratories Inc., Burlingame, Calif.) as the secondary antibody and detection system. Approximately 2×10$^6$ plaque forming units are screened in this manner.

Four positive plaques are selected from the first round of screening. These are subjected to a re-screen and plasmids (pBluescript) containing the cDNA inserts are rescued using a helper phage. The parent plasmid DNA is digested with the restriction endonucleases EcoRI and XhoI to release the cDNA inserts and analyzed by agarose gel electrophoresis one 1.6 Kb cDNA clone (designated Kcal 1.6) is selected for Northern hybridization, genomic Southern blotting and DNA sequencing. For Northern hybridization, mRNA is isolated from frozen rat tissues using "Fast Track" mRNA isolation kit (Invitrogen, San Diego, Calif.) or purchased from Clontech Labs (Palo Alto, Calif.). Genomic Southern blot, "Zoo-blot" is purchased from Clontech Labs and processed as described by the manufacturer. As shown in FIG. 5A, the cDNA Kcal 1.6 detects a single mRNA band of approximately 2.1 Kb in the adult rat brain mRNA (lane 1) bovine brain mRNA (lane 2) and porcine brain mRNA (lane 3). The probe, however, reveals two mRNA bands of 2.1 and 3.0 Kb in size in the northern blot of mRNA from neonatal rat brain (FIG. 5B). These results may indicate that in the neonatal rat brain, there are two distinct mRNA species which hybridize to Kcal 1.6, possibly arising from the alternate splicing of mRNA. Next, an EcoRI cut-genomic southern blot is probed with Kcal 1.6 cDNA. As shown in FIG. 6, after repeated washing of the blot at high stringency, the Kcal 1.6 probe detects a single 14 Kb band in human (lane 1) and in monkey (lane 2). However, there are variable patterns of hybridization in the rat (lane 3), mouse (lane 4), canine (lane 5), bovine (lane 6), rabbit (lane 7) and chicken (lane 8) ranging from 14 Kb to 3.0 Kb. There is no detectable hybridization with the yeast DNA (lane 9). These results indicate that there are notable homologies among the genes encoding p80 in various species.

8. Sequencing of Kcal 1.6

DNA sequencing is performed using the "Taq-Track" sequencing system (Promega Corp.) or the "Sequenase" system (U.S. Biochemical, Cleveland, Ohio). The nucleotide sequence obtained indicates that the clone is not full length, and lacks an initiation methionine residue. To obtain a full-length clone, Kcal 1.6 is used as a probe to screen the original porcine aorta cDNA library. Positive clones are analyzed by restriction mapping and electrophoresis for relatedness and insert size. One cDNA clone (designated Kcal 1.8) which is slightly longer than Kcal 1.6 is isolated and sequenced. The nucleotide and amino acid sequence of Kcal 1.8 is shown as SEQ ID NO. 1 and 2. The cDNA encodes 437 amino acids; the hydropathy plot (FIG. 7) indicates four strongly hydrophobic putative transmembrane domains. There is a putative calcium binding domain which closely matches that of the cloned cDNA slo encoding a putative calcium activated K-channel in Drosophila. However, there is no significant sequence homology between Kcal 1.8 and slo in other regions.

There is one strong consensus sequence in Kcal 1.8 for the cAMP dependent protein kinase, as well as those putative casein kinase phosphorylation sites. The Kcal 1.8 sequence has no significant homologies with any known voltage gated K-channels, sodium channels or calcium channels.

9. Expression of Kcal 1.8

CV-1 cells (ATCC CCL70) stably expressing the Kcal 1.8 gene product are produced by introducing the cDNA in the stable mammalian expression plasmid, pRc/CMV (InVitrogen) which contains a Neomarker. The Kcal 1.8 sequence is extracted from the pBluescript vector by digestion, with EcoRI and XhoI, and ligated into the corresponding sites of pRc/CMV. To transfect the cells, confluent 100 mm dishes of CV-1 cells are split and replated the day before the transfection, to ensure the cells are in log-growth phase. For electroporation, cells are harvested with trypsin, washed once with phosphate-buffered saline, and twice with an isotonic, low ionic strength buffer containing 272 mM sucrose, 7 mM sodium phosphate, pH 7.4 and 1 mM $MgCl_2$(buffer E). The cells are resuspended in this same buffer to a final concentration of $1.5 \times 10^6$ cells/mi. Twenty µg of the appropriate vector are digested with 40 units of ScaI for 2 hours at 37° C. to linearize the plasmid. The linearized plasmid is phenol/chloroform extracted, EtOH precipitated, and resuspended in 400 µl of Buffer E. The resuspended DNA is mixed with 400 ul of CV-1 cells ($1 \times 10^6$ cells) and incubated at room temperature for 2 minutes prior to electroporation. Electroporation is accomplished using a Bio-Rad gene pulser with a 300-V pulse at 25 µFarads. Transfections are done in duplicate. The suspension is allowed to further incubate for 5 minutes at room temperature, and then plated onto 100 mm tissue culture dishes with 10 mls of Dulbecco's modified Eagle's medium containing 10% fetal calf serum. Two days following transfection, G418 is added to a final concentration of 200 ug/ml. Isolated G418-resistant colonies are identified. They are selected with cloning cylinders and amplified.

Transfected cells are harvested and washed. They are incubated with [$^{125}$I]apamin in the binding buffer "B": Tris-HCl 10 mM, KCl 10 mM, pH 7.4, in the presence or absence of 1 uM cold apamin. The incubation is at 4° C. for 30 minutes with cold apamin, followed by 1 hour incubation at 4° C. with [$^{125}$I]apamin (20,000 cpm/well). Target cells are then filtered and washed with the binding buffer plus BSA. The filters are counted in a gamma counter.

Figure 8:
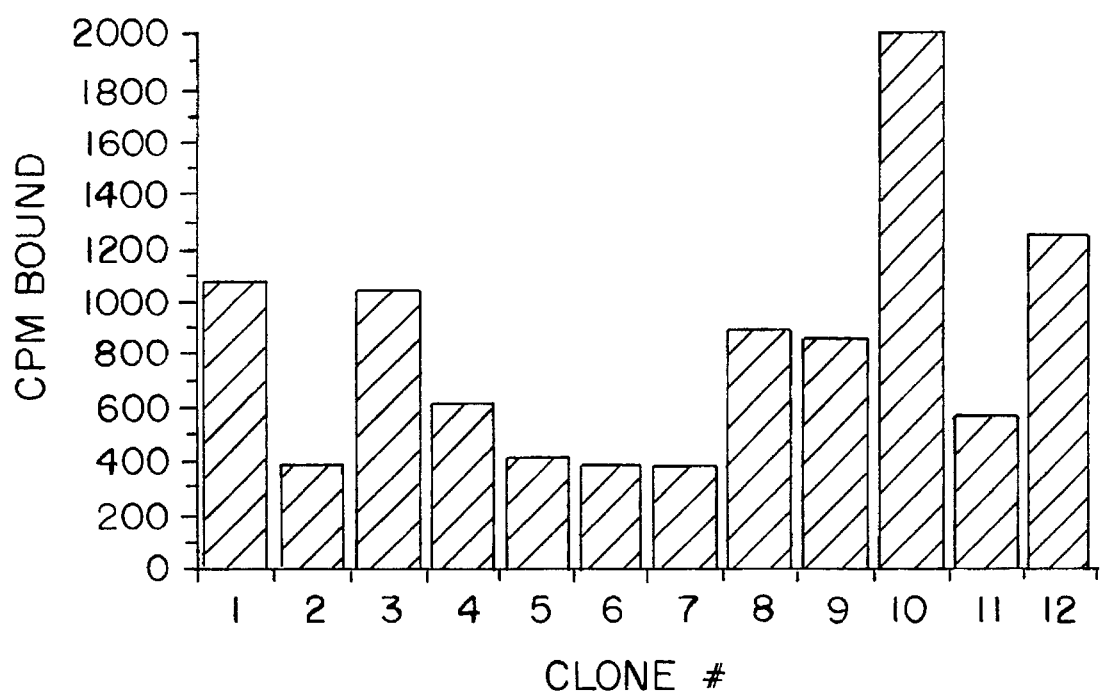
FIG. 8: Binding of apamin to plasma membrane of CV-1 cells transfected with Kcal 1.8 cDNA in a pRC/CMV vector.

As shown in FIG. 8, Transfectant #1, 3, 10 and 12 show significantly enhanced binding of [$^{125}$I]apamin, compared to other transfectants shown.

Those skilled in the art will recognize, or be able to ascertain using no more than routine experimentation, many equivalents to the specific embodiments of the invention described specifically herein. Such equivalents are intended to be encompassed in the scope of the following claims.

---

What we claim is:

1. An isolated and purified porcine apamin binding protein having a molecular weight of about 80 kilodaltons, wherein the protein is encoded by a nucleic acid which hybridizes under medium stringency conditions with a nucleic acid encoding the amino acid sequence of SEQ ID NO. 2, and wherein the protein is isolatable from porcine tissue.

2. The protein of claim 1 which is isolated from a porcine tissue selected from the group consisting of brain, heart, vascular smooth muscle, kidney, neuron, pancreas, melanoma and neuroblastoma.

3. The protein of claim 2 which is isolated from brain tissue.

4. The protein of claim 2 which is about 90–95% pure.

5. The protein of claim 1 which has the amino acid sequence of SEQ ID NO. 2.

6. An isolated and purified porcine apamin binding protein having a molecular weight of about 55 kilodaltons, wherein the protein is encoded by a nucleic acid which hybridizes under medium stringency conditions with a nucleic acid sequence encoding the amino acid sequence of SEQ ID NO. 2, and wherein the protein is isolatable from porcine tissue.

7. The protein of claim 6 which is isolated from a porcine tissue selected from the group consisting of brain, heart, vascular smooth muscle, kidney, neuron, pancreas, melanoma and neuroblastoma.

8. The protein of claim 7 which is isolated from brain tissue.

9. The protein of claim 7 which is about 90–95% pure.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1730 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 140..1456

( x i ) SEQUENCE DESCRIPTION: SEQ ID NO:1:

```
AGCAGCTCCA  TAGGCCCAGC  CCCGGCGTAC  AAGGATCACT  TCCGGTGGTA  CTTCACTACC        60

AAGAAGCTGC  GATTGGGCGA  GCGTGGAAGG  GGCATTTCCG  GTGTCCACCT  GCTTGGGTTC       120

TTTGGACAGA  AGTAGGAAG  ATG  GAG  CTC  GGC  GCC  GCG  GCC  CGT  GCT  TGG  TCG      172
                        Met  Glu  Leu  Gly  Ala  Ala  Ala  Arg  Ala  Trp  Ser
                         1              5                        10

CTC  TTG  TGG  CTG  CTG  CTT  CCC  TTG  CTT  GGC  CTG  GTC  GGC  GCC  AGC  GGT    220
Leu  Leu  Trp  Leu  Leu  Leu  Pro  Leu  Leu  Gly  Leu  Val  Gly  Ala  Ser  Gly
               15                        20                        25

CCC  CGT  ACC  TTA  GTG  CTT  CTG  GAC  AAC  CTC  AAC  CTG  CGG  GAG  ACG  CAT    268
Pro  Arg  Thr  Leu  Val  Leu  Leu  Asp  Asn  Leu  Asn  Leu  Arg  Glu  Thr  His
          30                        35                        40

TCA  CTT  TTC  TTC  CGG  AGC  CTA  AAG  GAT  CGG  GGC  TTC  GTA  CTC  ACA  TTC    316
Ser  Leu  Phe  Phe  Arg  Ser  Leu  Lys  Asp  Arg  Gly  Phe  Val  Leu  Thr  Phe
     45                        50                        55
```

```
AAG  ACC  GCA  GAT  GAC  CCC  AGC  CTG  TCC  CTG  ATT  AAG  TAC  GGA  GAG  TTC         364
Lys  Thr  Ala  Asp  Asp  Pro  Ser  Leu  Ser  Leu  Ile  Lys  Tyr  Gly  Glu  Phe
60                      65                      70                      75

CTC  TAT  GAC  AAT  CTC  ATC  GTC  TTT  TCA  CCT  TCG  GTA  GAA  GAT  TTT  GGA         412
Leu  Tyr  Asp  Asn  Leu  Ile  Val  Phe  Ser  Pro  Ser  Val  Glu  Asp  Phe  Gly
                    80                      85                      90

GGA  AAT  ATC  AAC  GTG  GAG  ACC  ATC  AGT  ACC  TTT  ATC  GAC  GGC  GGA  GGC         460
Gly  Asn  Ile  Asn  Val  Glu  Thr  Ile  Ser  Thr  Phe  Ile  Asp  Gly  Gly  Gly
               95                      100                     105

AGT  GTC  CTG  GTA  GCT  GCC  AGC  TCA  GAC  ATC  GGT  GAC  CCT  CTC  CGC  GAG         508
Ser  Val  Leu  Val  Ala  Ala  Ser  Ser  Asp  Ile  Gly  Asp  Pro  Leu  Arg  Glu
          110                     115                     120

CTG  GGC  AGT  GAG  TGT  GGG  ATT  GAG  TTT  GAC  GAG  GAG  AAA  ACG  GCC  GTC         556
Leu  Gly  Ser  Glu  Cys  Gly  Ile  Glu  Phe  Asp  Glu  Glu  Lys  Thr  Ala  Val
     125                     130                     135

ATT  GAC  CAT  CAC  AAC  TAT  GAT  GTC  TCA  GAC  CTC  GGC  CAG  CAC  ACG  CTC         604
Ile  Asp  His  His  Asn  Tyr  Asp  Val  Ser  Asp  Leu  Gly  Gln  His  Thr  Leu
140                     145                     150                     155

ATT  GTG  GCC  GAC  ACT  GAG  AAC  CTG  CTG  AAG  GCC  CCG  ACC  ATC  GTC  GGG         652
Ile  Val  Ala  Asp  Thr  Glu  Asn  Leu  Leu  Lys  Ala  Pro  Thr  Ile  Val  Gly
                    160                     165                     170

AAG  TCA  TCT  CTG  AAT  CCC  ATC  CTC  TTC  CGA  GGT  GTT  GGG  ATG  GTG  GCT         700
Lys  Ser  Ser  Leu  Asn  Pro  Ile  Leu  Phe  Arg  Gly  Val  Gly  Met  Val  Ala
               175                     180                     185

GAT  CCT  GAC  AAT  CCT  TTG  GTG  CTG  GAC  ATC  CTG  ACC  GGC  TCT  TCT  ACC         748
Asp  Pro  Asp  Asn  Pro  Leu  Val  Leu  Asp  Ile  Leu  Thr  Gly  Ser  Ser  Thr
          190                     195                     200

TCT  TAC  TCC  TTC  TTC  CCA  GAT  AAA  CCC  ATC  ACG  CAG  TAC  CCG  CAC  GCG         796
Ser  Tyr  Ser  Phe  Phe  Pro  Asp  Lys  Pro  Ile  Thr  Gln  Tyr  Pro  His  Ala
     205                     210                     215

GTG  GGG  AAG  AAC  ACG  CTG  CTC  ATC  GCG  GGG  CTG  CAG  GCC  CGG  AAC  AAC         844
Val  Gly  Lys  Asn  Thr  Leu  Leu  Ile  Ala  Gly  Leu  Gln  Ala  Arg  Asn  Asn
220                     225                     230                     235

GCC  CGT  GTC  ATC  TTC  AGC  GGC  TCC  CTC  GAC  TTC  TTC  AGC  GAT  GCC  TTC         892
Ala  Arg  Val  Ile  Phe  Ser  Gly  Ser  Leu  Asp  Phe  Phe  Ser  Asp  Ala  Phe
                    240                     245                     250

TTC  AAC  TCC  GCG  GTG  CAG  AAG  GCC  ACG  CCT  GGC  TCC  CAG  AGG  TAT  CCC         940
Phe  Asn  Ser  Ala  Val  Gln  Lys  Ala  Thr  Pro  Gly  Ser  Gln  Arg  Tyr  Pro
               255                     260                     265

CAG  ACA  GGC  AAC  TAT  GAG  CTC  GCC  GTG  GCC  CTC  TCC  CGC  TGG  GTG  TTC         988
Gln  Thr  Gly  Asn  Tyr  Glu  Leu  Ala  Val  Ala  Leu  Ser  Arg  Trp  Val  Phe
          270                     275                     280

AAG  GAG  GAG  GGT  GTC  CTC  CGA  GTG  GGG  CCT  GTG  TCC  CAC  CAT  CGG  GTG        1036
Lys  Glu  Glu  Gly  Val  Leu  Arg  Val  Gly  Pro  Val  Ser  His  His  Arg  Val
     285                     290                     295

GGC  GAG  AAA  GCC  CCA  CCC  AAC  GCC  TAC  ACC  GTC  ACT  GAC  CTA  GTC  GAG        1084
Gly  Glu  Lys  Ala  Pro  Pro  Asn  Ala  Tyr  Thr  Val  Thr  Asp  Leu  Val  Glu
300                     305                     310                     315

TAC  AGC  ATC  GTG  ATT  GAG  CAG  CTC  TCA  CAG  GGC  AGA  TGG  GTC  CCC  TTT        1132
Tyr  Ser  Ile  Val  Ile  Glu  Gln  Leu  Ser  Gln  Gly  Arg  Trp  Val  Pro  Phe
                    320                     325                     330

GAT  GGC  GAC  GAC  ATT  CAG  CTG  GAG  TTT  GTC  CGC  ATC  GAT  CCT  TTC  GTG        1180
Asp  Gly  Asp  Asp  Ile  Gln  Leu  Glu  Phe  Val  Arg  Ile  Asp  Pro  Phe  Val
               335                     340                     345

AGG  ACC  TTC  TTG  AAG  AGG  AAA  GGC  GGC  AAG  TAC  AGC  GTC  CAG  TTC  AAG        1228
Arg  Thr  Phe  Leu  Lys  Arg  Lys  Gly  Gly  Lys  Tyr  Ser  Val  Gln  Phe  Lys
          350                     355                     360

TTG  CCG  GAC  GTG  TAC  GGC  GTG  TTC  CAG  TTC  AAA  GTG  GAC  TAC  AAC  CGG        1276
Leu  Pro  Asp  Val  Tyr  Gly  Val  Phe  Gln  Phe  Lys  Val  Asp  Tyr  Asn  Arg
     365                     370                     375
```

```
CTG GGC TAC ACG CAC CTG TAC TCC TCC ACT CAG GTG TCC GTG CGG CCC              1324
Leu Gly Tyr Thr His Leu Tyr Ser Ser Thr Gln Val Ser Val Arg Pro
380                 385                 390                 395

CTG CAG GCA CAC GCA GTA CGA GCG CTT CAT CCC CTC GGC TTA CCC CTA              1372
Leu Gln Ala His Ala Val Arg Ala Leu His Pro Leu Gly Leu Pro Leu
                400                 405                 410

CTA CGC CAG CGC CTT CTC CAT GAT GGT CGG GCT CTT CAT CTT CAG CGT              1420
Leu Arg Gln Arg Leu Leu His Asp Gly Arg Ala Leu His Leu Gln Arg
            415                 420                 425

CGT CTT CTT GCA CAT GAA GGA GAA GGA GAA GTC TGACTGAGGG GCCGGGCCGG            1473
Arg Leu Leu Ala His Glu Gly Glu Gly Glu Val
        430                 435

GCCCCAGGAC TCCTTACAAC ACACAGGGAG GGTTTTTATA GGCTTGCCTT CCCCCCCCTT            1533

TATGGTGGGC TTTGTTTGTT TTTAAAGCCA CGGACAATGG CACAGCTTAC CTCAGTGGGA            1593

GATGCAAGAT GAGTACCAGG GGGTGGTTAG GAATAATTTC TAAGTTTTTC CACCTTGAAT            1653

GCTGAGTGGT ATTTTTCATA TGTAAAGTCA ACTGATTTCT AAAATAAAAG AAAAACATCA            1713

CCCTCAGAAA AAAAAAA                                                           1730
```

( 2 ) INFORMATION FOR SEQ ID NO:2:

( i ) SEQUENCE CHARACTERISTICS:
      ( A ) LENGTH: 438 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Met Glu Leu Gly Ala Ala Ala Arg Ala Trp Ser Leu Leu Trp Leu Leu
1               5                   10                  15

Leu Pro Leu Leu Gly Leu Val Gly Ala Ser Gly Pro Arg Thr Leu Val
            20                  25                  30

Leu Leu Asp Asn Leu Asn Leu Arg Glu Thr His Ser Leu Phe Phe Arg
        35                  40                  45

Ser Leu Lys Asp Arg Gly Phe Val Leu Thr Phe Lys Thr Ala Asp Asp
    50                  55                  60

Pro Ser Leu Ser Leu Ile Lys Tyr Gly Glu Phe Leu Tyr Asp Asn Leu
65                  70                  75                  80

Ile Val Phe Ser Pro Ser Val Glu Asp Phe Gly Gly Asn Ile Asn Val
                85                  90                  95

Glu Thr Ile Ser Thr Phe Ile Asp Gly Gly Gly Ser Val Leu Val Ala
                100                 105                 110

Ala Ser Ser Asp Ile Gly Asp Pro Leu Arg Glu Leu Gly Ser Glu Cys
            115                 120                 125

Gly Ile Glu Phe Asp Glu Glu Lys Thr Ala Val Ile Asp His His Asn
    130                 135                 140

Tyr Asp Val Ser Asp Leu Gly Gln His Thr Leu Ile Val Ala Asp Thr
145                 150                 155                 160

Glu Asn Leu Leu Lys Ala Pro Thr Ile Val Gly Lys Ser Ser Leu Asn
                165                 170                 175

Pro Ile Leu Phe Arg Gly Val Gly Met Val Ala Asp Pro Asp Asn Pro
            180                 185                 190

Leu Val Leu Asp Ile Leu Thr Gly Ser Ser Thr Ser Tyr Ser Phe Phe
        195                 200                 205

Pro Asp Lys Pro Ile Thr Gln Tyr Pro His Ala Val Gly Lys Asn Thr
    210                 215                 220
```

| | | | | | | | | | | | | | |
|---|---|---|---|---|---|---|---|---|---|---|---|---|---|
| Leu 225 | Leu | Ile | Ala | Gly | Leu 230 | Gln | Ala | Arg | Asn | Asn 235 | Ala | Arg | Val | Ile | Phe 240 |
| Ser | Gly | Ser | Leu | Asp 245 | Phe | Phe | Ser | Asp | Ala 250 | Phe | Phe | Asn | Ser | Ala 255 | Val |
| Gln | Lys | Ala | Thr 260 | Pro | Gly | Ser | Gln | Arg 265 | Tyr | Pro | Gln | Thr | Gly 270 | Asn | Tyr |
| Glu | Leu | Ala 275 | Val | Ala | Leu | Ser | Arg 280 | Trp | Val | Phe | Lys | Glu 285 | Glu | Gly | Val |
| Leu | Arg 290 | Val | Gly | Pro | Val | Ser 295 | His | His | Arg | Val | Gly 300 | Glu | Lys | Ala | Pro |
| Pro 305 | Asn | Ala | Tyr | Thr | Val 310 | Thr | Asp | Leu | Val | Glu 315 | Tyr | Ser | Ile | Val | Ile 320 |
| Glu | Gln | Leu | Ser | Gln 325 | Gly | Arg | Trp | Val | Pro 330 | Phe | Asp | Gly | Asp | Asp 335 | Ile |
| Gln | Leu | Glu | Phe 340 | Val | Arg | Ile | Asp | Pro 345 | Phe | Val | Arg | Thr | Phe 350 | Leu | Lys |
| Arg | Lys | Gly 355 | Gly | Lys | Tyr | Ser | Val 360 | Gln | Phe | Lys | Leu | Pro 365 | Asp | Val | Tyr |
| Gly | Val 370 | Phe | Gln | Phe | Lys | Val 375 | Asp | Tyr | Asn | Arg | Leu 380 | Gly | Tyr | Thr | His |
| Leu 385 | Tyr | Ser | Ser | Thr | Gln 390 | Val | Ser | Val | Arg | Pro 395 | Leu | Gln | Ala | His | Ala 400 |
| Val | Arg | Ala | Leu | His 405 | Pro | Leu | Gly | Leu | Pro 410 | Leu | Leu | Arg | Gln | Arg 415 | Leu |
| Leu | His | Asp | Gly 420 | Arg | Ala | Leu | His | Leu 425 | Gln | Arg | Arg | Leu | Leu 430 | Ala | His |
| Glu | Gly | Glu 435 | Gly | Glu | Val | | | | | | | | | | |